United States Patent [19]
Oroszlan et al.

[11] Patent Number: 5,252,477
[45] Date of Patent: Oct. 12, 1993

[54] HUMAN IMMUNODEFICIENCY VIRUS SPECIFIC PROTEOLYTIC ENZYME AND A METHOD FOR ITS SYNTHESIS AND RENATURATION

[75] Inventors: Stephen Oroszlan, Potomac; Terry D. Copeland, Frederick, both of Md.

[73] Assignee: The United States of America as represented by the United States Department of Health and Human Services, Bethesda, Md.

[21] Appl. No.: 57,183

[22] Filed: Jun. 1, 1987

[51] Int. Cl.$^5$ .......................... C12N 9/50; C12N 7/04; C12N 15/84

[52] U.S. Cl. .................................. 435/219; 435/235.1; 435/236; 530/389.1; 530/389.4; 536/23.2

[58] Field of Search ...................... 435/212, 219, 235.1, 435/236, 948; 935/3, 5; 536/27, 23.2; 530/388.26, 389.4, 389.1

[56] References Cited

PUBLICATIONS

Oroszlan, S. et al, "Primary Structure and Processing of gag and env Gene Products of Human T-Cell Leukemia Viruses HTLV-I$_{CR}$ and HTLV-I$_{ATK}$, Current Topics in Microbiology and Immunology", vol. 115, pp. 221-233, 1985.

Copeland, T. D., "A Synthetic Dodecapeptide Substrate for Type C RNA Tumor Virus Associated Proteolytic Enzyme", PEPTIDES: Synthesis-Structure-Function, Pierce Chemical Company, 1981; pp. 497-550.

Yoshinaka et al, "Murine Leukemia Virus Protease Is Encoded By the gag-pol Gene and is Synthesized Through Suppression of an Amber Termination Condon", Proc. Natl. Acad. Sci., USA, vol. 82, pp. 1618-1622, Mar. 1985.

Henderson, et al, "Analysis of Proteins and Peptides Purified From Sucrose Gradient Banded HTLV-III, UCLA Symposia on Molecular and Cellular Biology"; New Series, vol. 71, pp. 135-147, May 1988.

Yoshinaka, Y., et al. (1985) J. Virol. 55(3), 870-873.

Yoshinaka, Y., et al. (1986) J. Virol. 57(3), 826-832.

Ratner, et al. (1985) Nature 313, 277-284.

Debouck C., et al. (1987) Proc. Natl. Acad. Sci., USA 84, 8903-8906.

*Primary Examiner*—Charles L. Patterson, Jr.
*Attorney, Agent, or Firm*—Knobbe, Martens, Olson & Bear

[57] ABSTRACT

HIV protease necessary for the natural synthesis of HIV has been identified and sequenced. Rabbit antiserum against the C-terminal portion of HIV protease has been produced and used to isolate natural HIV protease and characterize its activity. In addition, a method for producing synthetic HIV protease having the correct stereospecific conformation and specific HIV proteolytic activity has been achieved.

6 Claims, 5 Drawing Sheets

HTLV-III BH10

|→ protease

| | |
|---|---|
| GlnGlyThrValSerPheAsnPhe<u>ProGlnIle</u>ThrLeuTrpGln | 7 |
| ArgProLeuValThrIleLysIleGlyGlyGlnLeuLysGluAla | 22 |
| LeuLeuAspThrGlyAlaAspAspThrValLeuGluGluMetSer | 37 |
| LeuProGlyArgTrpLysProLysMetIleGlyGlyIleGlyGly | 52 |
| PheIleLysValArgGlnTyrAspGlnIleLeuIleGluIleCys | 67 |
| GlyHisLysAlaIleGlyThrValLeuValGlyProThrProVal | 82 |
| AsnIleIleGlyArgAsnLeuLeuThrGlnIleGlyCysThrLeu | 97 |

|→ RT

AsnPhe<u>ProIleSerPro</u>IleGluThrValProValLysLeuLys

FIGURE 1

CONSERVED SEQUENCES OF RETROVIRAL PROTEASES

| | 1 | 17 | 30 | 56 | 87 | 92 | 125 | CLEAVAGE SITE SPECIFICITY |
|---|---|---|---|---|---|---|---|---|
| M-MuLV | ⊢ | RIT | LVDTGA | GATG | DC | LLGRD | ⊣ | a |
| AKR | | ... | ...... | .... | .. | ..... | | a |
| FeLV | | ... | ...... | .... | .. | ..... | | a |
| BaEV | | ... | ...... | .... | .. | ..... | | a |
| HTLV-I,-II | | ... | ...... | .... | S. | ..... | | a |
| BLV | | SGP | ...... | GAGG | KI | ..... | | b |
| VISNA | | IKV | ...... | IGGI | SP | ..... | | c |
| EIAV | | IND | ...... | TGII | VA | ..... | | d |
| HTLV-III | | LVT | ...... | GGTI | VN | ..... | | e |

| | P4 | P3 | P2 | P1 | |
|---|---|---|---|---|---|
| a | S | S | L | Y | · P |
| b | P | A | I | L | · P |
| c | R | E | V | Y | · P |
| d | S | E | E | Y | · P |
| e | S | Q | N | Y | · P |

DOTS REPRESENT IDENTICAL RESIDUES

| | | | | | | | | | | |
|---|---|---|---|---|---|---|---|---|---|---|
| BH 10 | CAG Gln | ACC Thr | AGA Arg | GCC Ala | AAC Asn | AGC Ser | CCC Pro | ACC Thr | AGA Arg | GAG Glu | CTT Leu | CAG Gln | GTC Val | TGG Trp | GGT Gly | AGA Arg | GAC Asp | AAC Asn | TCC Ser | CCC Pro | TCA Ser | GAA Glu | GCA Ala |  1796 488 / 56 |
| | | | | | | | | | | | | |→PROTEASE | | | | | | | | | | | |
| BH 10 | GGA Gly | GCC Ala | GAT Asp | AGA Arg | CAA Gln | GAT Asp | ATA Ile | GAA Glu | ACT Thr | GTA Val | CTT Leu | GAA Glu | GAA Glu | CAA Gln | CTT Leu | CGG Arg | CAA Gln | TCC Ser | TTT Phe | AAC Asn | TGC Cys | CCT Pro | ATC Ile | GTC Val | ACA Thr | ATA Ile | 1871 512 / 81 |
| BH 10 | AAG Lys | ATA Ile | GGG Gly | GGG Gly | CAA Gln | CTA Leu | AAG Lys | GAA Glu | GCT Ala | CTA Leu | TTA Leu | GAT Asp | ACA Thr | GGA Gly | GCT Ala | GAT Asp | GAT Asp | ACA Thr | GTA Val | TTA Leu | GAA Glu | GAA Glu | ATG Met | AGT Ser | TTG Leu | 1946 106 |
| BH 10 | CCA Pro | GGA Gly | AGA Arg | TGG Trp | AAA Lys | CCA Pro | AAA Lys | ATG Met | ATA Ile | GGG Gly | GGT Gly | ATT Ile | GGA Gly | GGT Gly | TTT Phe | ATC Ile | AAA Lys | GTA Val | AGA Arg | CAG Gln | TAT Tyr | GAT Asp | CAG Gln | ATA Ile | CTC Ile | ATA Ile | 2021 131 |
| BH 10 | ATA Ile | GAA Glu | ATC Ile | TGT Cys | GGA Gly | CAT His | AAA Lys | GCT Ala | ATA Ile | GGT Gly | ACA Thr | GTA Val | TTA Leu | GTA Val | GGA Gly | CCT Pro | ACA Thr | CCT Pro | GTC Val | AAC Asn | ATA Ile | ATT Ile | GGA Gly | AGA Arg | AAT Asn | 2096 156 |
| | | | | | | | | | | | | | | | |→RT | | | | | | | | | | | |
| BH 10 | CTG Leu | TTG Leu | ACT Thr | CAG Gln | TGC Cys | ATT Ile | TTT Phe | CCC Pro | ATT Ile | AGC Ser | CCT Pro | ATT Ile | GAG Glu | ATT Ile | GTA Val | CCA Pro | GTA Val | AAA Lys | TTA Leu | AAG Lys | CCA Pro | GGA Gly | ATG Met | GAT Asp | GGC Gly | 2171 181 |
| BH 10 | GGA Gly | ATG Met | GAT Asp | GGC Gly | CCA Pro | AAA Lys | GTT Val | AAA Lys | CAA Gln | TGG Trp | CCA Pro | TTG Leu | ACA Thr | GAA Glu | GAA Glu | AAT Asn | CCA Pro | TAC Tyr | AAT Asn | ACT Thr | GCC Ala | ATT Ile | TTT Phe | GAC Asp | TTC Phe | 2246 206 |
| BH 10 | GAA Glu | ATG Met | GAA Glu | GAC Asp | ACT Thr | TTT Phe | AGA Arg | AAA Lys | TAC Tyr | ACT Thr | GTA Val | ACA Thr | GAA Glu | ATA Ile | AAA Lys | GAA Glu | TTT Phe | AGA Arg | AAG Lys | CAA Gln | AAT Asn | GAC Asp | AAA Lys | TGG Trp | AGA Arg | AAA Lys | 2321 231 |
| BH 10 | AAA Lys | AAA Lys | GAC Asp | AGT Ser | ACT Thr | AAA Lys | TGG Trp | AGA Arg | AAA Lys | TTA Leu | GTA Val | GAT Asp | TTC Phe | AGA Arg | GAA Glu | CTT Leu | AAT Asn | AAG Lys | AGA Arg | ACT Thr | CAA Gln | GAC Asp | TTC Phe | TGG Trp | GAA Glu | 2396 256 |
| BH 10 | GTT Val | CAA Gln | TTA Leu | GGA Gly | ATA Ile | CCA Pro | CAT His | CCC Pro | GCA Ala | GGG Gly | TTA Leu | AAA Lys | AAG Lys | AAA Lys | AAA Lys | TCA Ser | GTA Val | ACA Thr | GTA Val | CTG Leu | GAT Asp | GTG Val | GGT Gly | GAT Asp | GCA Ala | 2471 281 |
| BH 10 | TAT Tyr | TTT Phe | TCA Ser | GTT Val | CCC Pro | TTA Leu | GAT Asp | GAA Glu | GAC Asp | TTC Phe | AGG Arg | AAG Lys | TAT Tyr | ACT Thr | GCA Ala | TTT Phe | ACC Thr | ATA Ile | CCT Pro | AGT Ser | ATA Ile | AAC Asn | AAT Asn | GAG Glu | ACA Thr | 2546 306 |

HUMAN IMMUNODEFICIENCY VIRUS SPECIFIC PROTEOLYTIC ENZYME AND A METHOD FOR ITS SYNTHESIS AND RENATURATION

BACKGROUND OF THE INVENTION

We conducted research which identified and structurally, biochemically and enzymologically characterized human immunodeficiency virus (HIV) protease, as well as its natural polyprotein substrates, in order to develop drugs that inhibit protease activity. It was known from our work on protease deficient MuLV mutants that when precursor polyproteins are not cleaved mature infectious virus can not be produced. Instead, non-infectious particles are made that, however, remain immunogenic because they carry complete envelopes. The idea underlying this research was to ultimately prepare chemical inhibitors that penetrate the infected cell, become incorporated into the budding virus, bind with high affinity to the viral protease or precursor polyproteins, prevent cleavage and lead to the production of non-infectious but still immunogenic viral progeny. The use of these chemical inhibitors would block the spread of HIV infection while allowing for antigenic stimulation of host immunity.

SUMMARY OF THE INVENTION

We have identified the amino acid sequence that constitutes human immunodeficiency virus (HIV) protease, a proteolytic enzyme specific for the virus known as HIV, LAV and HTLV-III. This enzyme is necessary in the natural synthesis of HIV in the cells of subjects infected by the virus. In the course of natural synthesis it is necessary for protein of the virus to be lysed from precursor proteins. It is this function for which the proteolytic enzyme we have identified and synthesized is specific. Without HIV protease the active virus cannot be reproduced in infected cells and the natural synthesis process will be stopped short of completion. As a result, with our discovery of the structure of this specific protease and our synthesis of the active enzyme, a protease inhibitor specific for this enzyme can be designed.

BRIEF DESCRIPTION OF THE FIGURES

FIG. 1 provides the amino acid sequence of the HIV protease.

FIG. 2 illustrates the regions of sequence conservation between a number of different retroviral proteases.

FIG. 3 provides a portion of the DNA sequence of HIV containing the coding region for the HIV protease.

FIG. 4 is a graphic representation of the chromatographic separation of various substrates before and after cleavage with the synthetic HIV protease.

DESCRIPTION OF THE PREFERRED EMBODIMENTS

Figure 4A:
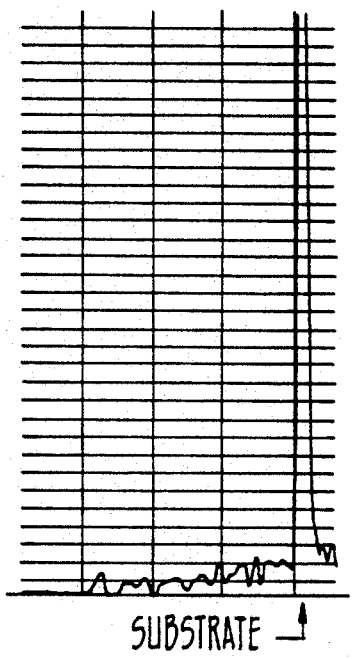
FIGS. 4a and 4b illustrate cleavage of MuLV synthetic peptides before and after addition of the HIV protease.

The DNA sequence coding for HIV was known. As we had previously identified proteases specific for human retroviruses, and we had identified homologies in the sequences coding for proteases necessary in the natural synthesis of these other retroviruses, we were able to identify sections in the DNA sequence coding for HIV proteins that should be within the sequence coding for a protease specific for HIV and necessary for its natural synthesis. (Copeland and Oroszlan, "A Synthetic Dodecapeptide Substrate For Type C RNA Tumor Virus Associated Proteolytic Enzyme," *PEPTIDES: Synthesis-Structure-Function*, Pierce Chemical Company, 1981, and Yoshinaka et al, "Murine Leukemia Virus Protease Is Encoded By The gag-pol Gene and Is Synthesized Through Suppression of an Amber Termination Codon", *Proc. Natl. Acad. Sci., USA*, Vol. 82, pages 1618-1622, March 1985, included herein in their entirety by reference). Our previous work indicated to us that certain sequences were conserved in retroviral proteases; these are set forth in FIG. 2.

HIV protease is a 99 amino acid peptide, which has a molecular weight of 11K-11.5K daltons measured by SDS PAGE. The amino acid sequence is given in FIG. 1, as marked, beginning with ProGlnIle . . . . FIG. 3 indicates the position in the 99 amino acid peptide in the HIV sequence. The peptide sequence is shown in the third line in each grouping. The first line in each grouping is the DNA sequence coding for the HIV protease. The second line in each grouping is an alternative amino acid sequence, which is correct for the expression of certain portions of HIV protein. However, due to a reading frame shift prior to the protease, the sequence we have identified in the third line and repeated in FIG. 1, is the actual amino acid sequence of the protease. After identifying the amino acid sequence for HIV protease, we synthesized the C-terminal peptide consisting of 15 amino acids (IleGlyArgAsnLeuLeuThrGlnIleGlyCysThrLeuAsPhe). With this 15 amino acid synthetic peptide we generated a rabbit antiserum. The rabbit antiserum was then used to isolate the natural protease from HIV. The activity of the natural protease was identified and confirmed by cleaving natural proteins in natural virus substrates and in synthetic substrates characteristic of all retroviruses and, therefore, characteristic of cleavage sites in HIV itself. This assay was conducted according to the method discussed in Copeland and Oroszlan (supra), essentially by incubating the substrate with the suspected protease, and then separating using PAGE and HPLC procedures.

Having confirmed that the sequence we identified was for HIV protease, we proceeded by solid phase synthesis using the Merrifield method to synthesize the 99 amino acid peptide (Merrifield R. B. (1963), "Solid Phase Peptide Synthesis I". *J. Amer. Chem. Soc.* 85, 2149-2154, included herein by reference). The synthesis was done using the semiautomatic synthesis procedures with an Applied Biosystems program and an Applied Biosystems 430 Peptide synthesizer (Foster City, Calif.).

After synthesis, the peptide was removed from the resin on which it was constructed and blocking groups were eliminated from the synthetic peptide by conventional procedures. The synthetic protease was then recovered and purified.

As synthesized, the peptide is linear and demonstrates no activity as a proteolytic enzyme. In addition to removing blocking groups, therefore, it was necessary to convert the protease to its natural stereospecific conformation in order to exhibit proteolytic activity. As produced, the synthetic HIV protease was extracted in a strong acid. It was necessary, thereafter, to submit it to treatment and purification using specific buffer systems and dialysis. Thereafter, we proceeded by trial and error to effect renaturation and to refold the peptide into its natural stereospecific confirmation. This was done through recovery in guanidine hydrochloride solution, concentration, recovery of all solutes and recovery in an aqueous solution. The proper folding was accomplished through a series of trial and error steps. The correct folding of the peptide is the result of intra and intermolecular forces and bonding, and of the characteristics of the media to which we subjected the synthetic peptide.

Figure 4C:
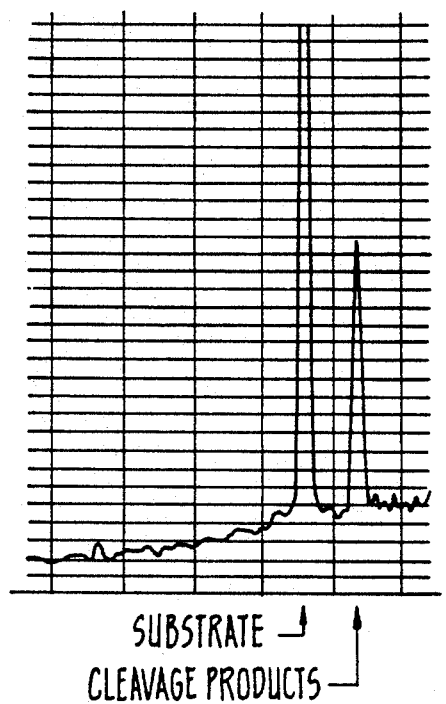
FIGS. 4c and 4d illustrate cleavage of the MuLV substrate using cathepsin D and renin respectively.
Figure 4B:
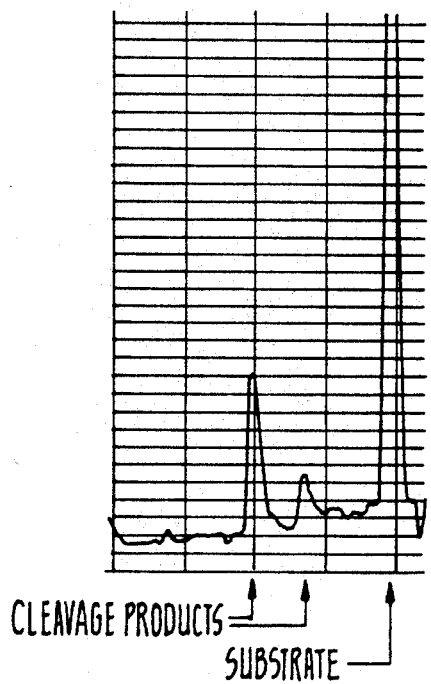
Figure 4D:
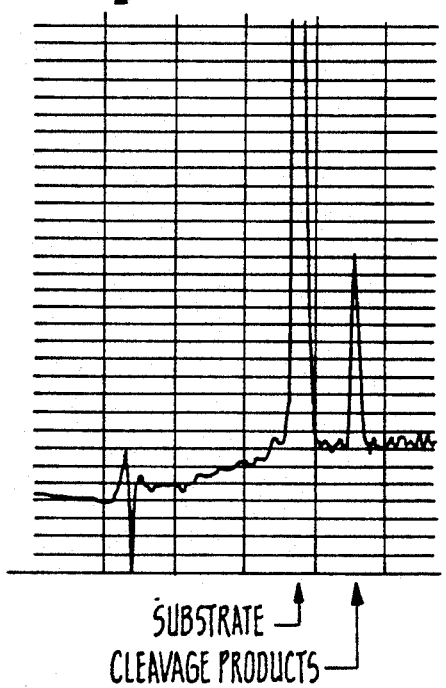
Figure 4E:
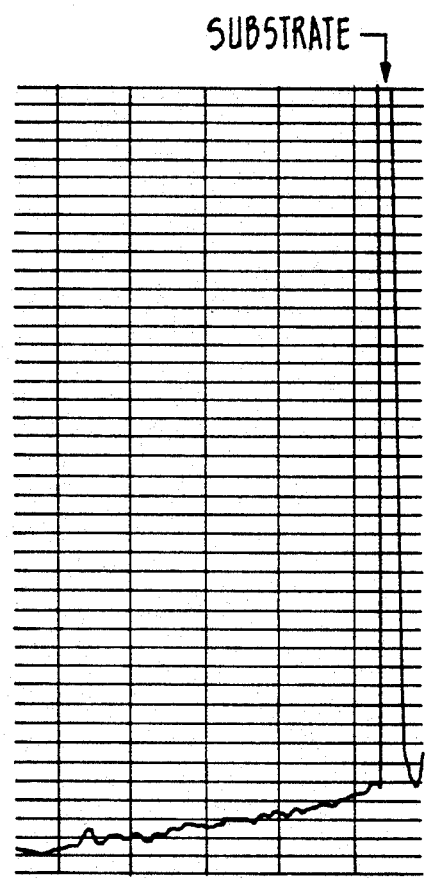
FIGS. 4e and 4f illustrate cleavage of an HIV peptide substrate before and after incubation with the HIV protease.
Figure 4F:
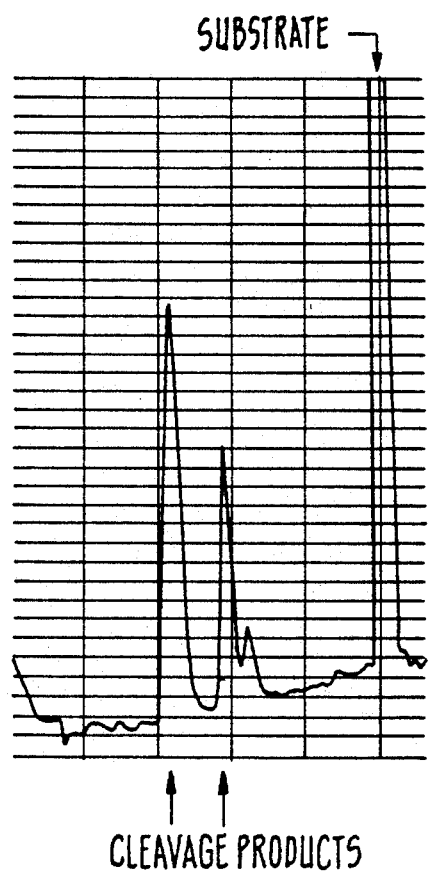

We were able to obtain a synthetic protein that showed specific proteolytic activity for HIV. Assays to confirm that we had produced the active peptide were conducted by incubating the synthetic protease with natural viral substrates and with synthetic viral substrates. The results demonstrated that our synthetic HIV protease was specific for the characteristic cleavage sites. The assay methods are described in Oroszlan and Copeland, UCLA Symposium on Molecular and Cellular Biology (included herein by reference). This activity is illustrated in FIG. 4. FIG. 4a illustrates MuLV synthetic peptides containing the known proteolytic cleavage site. FIG. 4b shows the same peptide after being incubated with our synthetic HIV protease. The two peaks to the left of the main peptide indicate products of cleavage of the MuLV substrate. FIGS. 4c and 4d illustrate cleavage of the same substrate using two other proteases, cathepsin D and renin, respectively. As can be seen from the products to the right of the substrate peak, those enzymes cleave the substrate at different cleavage site. FIG. 4e shows a synthetic HIV peptide substrate. FIG. 4f illustrates the results after incubation after our synthetic HIV protease. The products indicated by the peaks to the left of the substrate peak demonstrate proteolysis activity.

We claim:

1. An isolated proteolytic enzyme comprising the amino acid sequence:

| | |
|---|---|
| ProGlnIleThrLeuTrpGln | 7 |
| ArgProLeuValThrIleLysIleGlyGlyGlnLeuLysGluAla | 22 |
| LeuLeuAspThrGlyAlaAspAspThrValLeuGluGluMetSer | 37 |
| LeuProGlyArgTrpLysProLysMetIleGlyGlyIleGlyGly | 52 |
| PheIleLysValArgGlnTyrAspGlnIleLeuIleGluIleCys | 67 |
| GlyHisLysAlaIleGlyThrValLeuValGlyProThrProVal | 82 |
| AsnIleIleGlyArgAsnLeuLeuThrGlnIleGlyCysThrLeu AsnPhe | 97 |

2. Peptides corresponding to at least 10 contiguous amino acids derived from the sequence coding for the proteolytic enzyme of claim 1.

3. A proteolytic enzyme comprising the sequence of claim 1 prepared by synthetic means in a stereospecific conformation that provides human immunodeficiency virus proteolytic activity.

4. A method for making the proteolytic enzyme of claim 3 comprising:
   obtaining the amino acid sequence of claim 9;
   synthesizing said proteolytic enzyme, corresponding to said amino acid sequence, in a cell free system; and
   isolating said enzyme in a substantially pure form.

5. A Polyclonal antibody preparation immunoreactive with the protein corresponding to the amino acid sequence of claim 1.

6. A DNA sequence coding for the proteolytic enzyme of claim 1.

* * * * *

UNITED STATES PATENT AND TRADEMARK OFFICE
CERTIFICATE OF CORRECTION

PATENT NO. : 5,252,477
DATED : October 12, 1993
INVENTOR(S) : Oroszlan et al

It is certified that error appears in the above-indentified patent and that said Letters Patent is hereby corrected as shown below:

In claim 4, line 3, delete [claim 9] and insert -- claim 1 --.

Signed and Sealed this

Sixteenth Day of November, 1999

Attest:

Q. TODD DICKINSON

*Attesting Officer*    *Acting Commissioner of Patents and Trademarks*